US005279603A

United States Patent [19]

Everett et al.

[11] Patent Number: 5,279,603

[45] Date of Patent: Jan. 18, 1994

[54] COLLAPSIBLE UROLOGY DRAIN PAN ASSEMBLY WITH RETENTION MECHANISM

[75] Inventors: Dennis K. Everett, Garfield Heights; Victor J. Hrdlicka, Mayfield Heights, both of Ohio

[73] Assignee: Picker International, Inc., Cleveland, Ohio

[21] Appl. No.: 43,618

[22] Filed: Apr. 7, 1993

Related U.S. Application Data

[63] Continuation of Ser. No. 844,124, Mar. 2, 1992, abandoned, which is a continuation-in-part of Ser. No. 615,878, Nov. 20, 1990, Pat. No. 5,092,859.

[51] Int. Cl.[5] .............................................. A61M 1/00

[52] U.S. Cl. .................................. 604/322; 128/760; 220/482

[58] Field of Search ........................ 604/322; 128/760; 220/480-482, 657, 659; 5/503; 232/433; 24/67.9, 67.11, 552, 532, 562-563; 248/99-101, 221.4; 211/71, 89

[56] References Cited

U.S. PATENT DOCUMENTS

| | | | |
|---|---|---|---|
| 3,346,883 | 10/1967 | Ersek | 604/322 |
| 4,592,582 | 6/1986 | Lavender et al. | 604/322 |
| 4,669,152 | 6/1987 | Alexander | 24/562 |
| 4,773,768 | 9/1988 | Leeper | 604/322 |
| 4,936,836 | 6/1990 | Weickgenannt | 604/332 |
| 4,997,104 | 3/1991 | Pohl | 24/563 |
| 5,078,705 | 1/1992 | Edwards et al. | 604/322 |
| 5,092,487 | 3/1992 | Richer et al. | 220/482 |
| 5,097,975 | 3/1992 | Waterston et al. | 220/482 |

FOREIGN PATENT DOCUMENTS

| | | | |
|---|---|---|---|
| 0191958 | 8/1988 | Japan | 604/322 |

*Primary Examiner*—Randall L. Green
*Assistant Examiner*—Gina M. Gualtieri
*Attorney, Agent, or Firm*—Timothy B. Gurin

[57] ABSTRACT

A one piece self-supporting collapsible plastic urology drain bag 24 is mounted to an examination end 14 of a urology table 10. The pan includes a vertical inner end wall 28, a sloping outer end wall 34, a pair of opposite side wall 30, 32, and a bottom wall 36 through which a drain port 38 is defined. The inner end wall 28 of the drain pan is secured between plates 50 and 52. The drain bag is sufficiently flexible to allow a physician to collapse the outer end wall 34 against inner end wall 28 yet with sufficient plastic memory to enable the drain pan to return to its non-flexed position when the collapsing force is removed. A retaining means 56 is disposed on each end of the upper edge of plate 52. Each retaining means comprises a support means 58 and pin 60 arrangement. The pins 60 extend inwardly from their respective support means 58 along a line generally parallel to the upper edge of plate 52 away from the inner end wall 28, and sufficiently spaced from each other, such that outer end wall 34 can be releasably engaged between pins 60 and the inner end wall 28.

18 Claims, 3 Drawing Sheets

COLLAPSIBLE UROLOGY DRAIN PAN ASSEMBLY WITH RETENTION MECHANISM

This application is a continuation of copending application Ser. No. 07/844,124, filed on Mar. 2, 1992, now abandoned, which is a continuation-in-part of application Ser. No. 07/615,878 filed on Nov. 20, 1990 titled One Piece, Collapsible Urology Drain, now U.S. Pat. No. 5,092,859.

FIELD OF THE INVENTION

The present invention relates to collapsible urology drain pan assemblies and means for retaining the drain pan in a collapsed position.

BACKGROUND OF THE INVENTION

Everett, et al.; U.S. patent application Ser. No. 07/615,878 titled One Piece, Collapsible Urology Drain Pan, is expressly incorporated herein by reference.

In the past, rigid, stainless steel drain pans were connected to one end of a urology examination table to capture urine, fluids used during irrigation, tissue dislodged during urological procedures, and the like. One of the problems with rigid urology pans is that they were mounted on the examination end of the table, i.e., between the physician and the patient. The physician frequently found it necessary to lean into and reach across the drain pan during examinations and procedures. The rigid pans were uncomfortable to the physician and interfered with performance of medical procedures.

Another urology drain arrangement is illustrated in U.S. Pat. No. 4,936,836. In this patent, a complex arrangement of stainless steel frame pieces are pivotally interconnected and biased into an open rectangle by springs in the hinges. A disposable, light weight, flexible urology bag is hung on and supported by the pivotal frame members.

In another arrangement, a flexible steel band is mounted to the end of the urology table. A light weight, disposable urology bag is hung from and supported by the steel band.

In Everett, et al., U.S. patent application referenced above, yet another arrangement is illustrated. A one piece collapsible plastic urology drain pan is used in place of the above pivotal frame or steel band and bag arrangements.

One of the problems with the collapsible, flexible or pivotal urology drain pan arrangements described above is that no means is provided to secure these arrangements in a collapsed position. This is desirable so that the examiner can move freely about in the space previously occupied by the drain pan arrangement without having to maintain constant pressure against the arrangement.

The present invention contemplates a collapsed urology drain assembly securing means which overcomes the above-referenced problem and others.

SUMMARY OF THE INVENTION

In accordance with one aspect of the present invention, a one piece, plastic urology drain pan is provided. The pan is constructed of a sufficiently strong, stiff plastic that is self-supporting, yet sufficiently flexible at least along its vertical sides that as the physician leans forward, the pan flattens and has less horizontal extension.

The drain pan has a rigid mounting assembly along an inner elongated end for mounting to a urology table. Outward extending sides have an outward flange adjacent the top which permits the side portions to fold along a generally vertical axis along a U-shaped horizontal cross section. An outer elongated end has a rolled, more rigid flange which is engaged by the physician as the physician leans forward.

Two horizontal pins are disposed at the top of the rigid mounting assembly. The pins are spaced such that both ends of the rolled outer elongated end of the urology drain pan can be releasably engaged behind the pins to hold the bag in close proximity to the table end. This provides the examiner with additional unrestricted space in the examination area.

The advantage of the present invention is that it provides a means of holding collapsible urology drain arrangements in a collapsed position. The advantage of this configuration is that it allows the examiner to move freely about in the space previously occupied by the drain pan arrangement without having to maintain constant pressure against the arrangement.

Another advantage of the present invention is that the physician can secure the drain arrangement in a collapsed position by use of the elbows thereby keeping the physician's hands sterile.

Still further advantages of the present invention will become apparent to those of ordinary skill in the art upon reading and understanding the following detailed description.

BRIEF DESCRIPTION OF THE DRAWINGS

The invention may take form in various parts and arrangements of parts, and in various steps or arrangements of steps. The drawings are only for purposes of illustrating a preferred embodiment and are not to be construed as limiting the invention.

DETAILED DESCRIPTION OF THE PREFERRED EMBODIMENT

Figure 1:
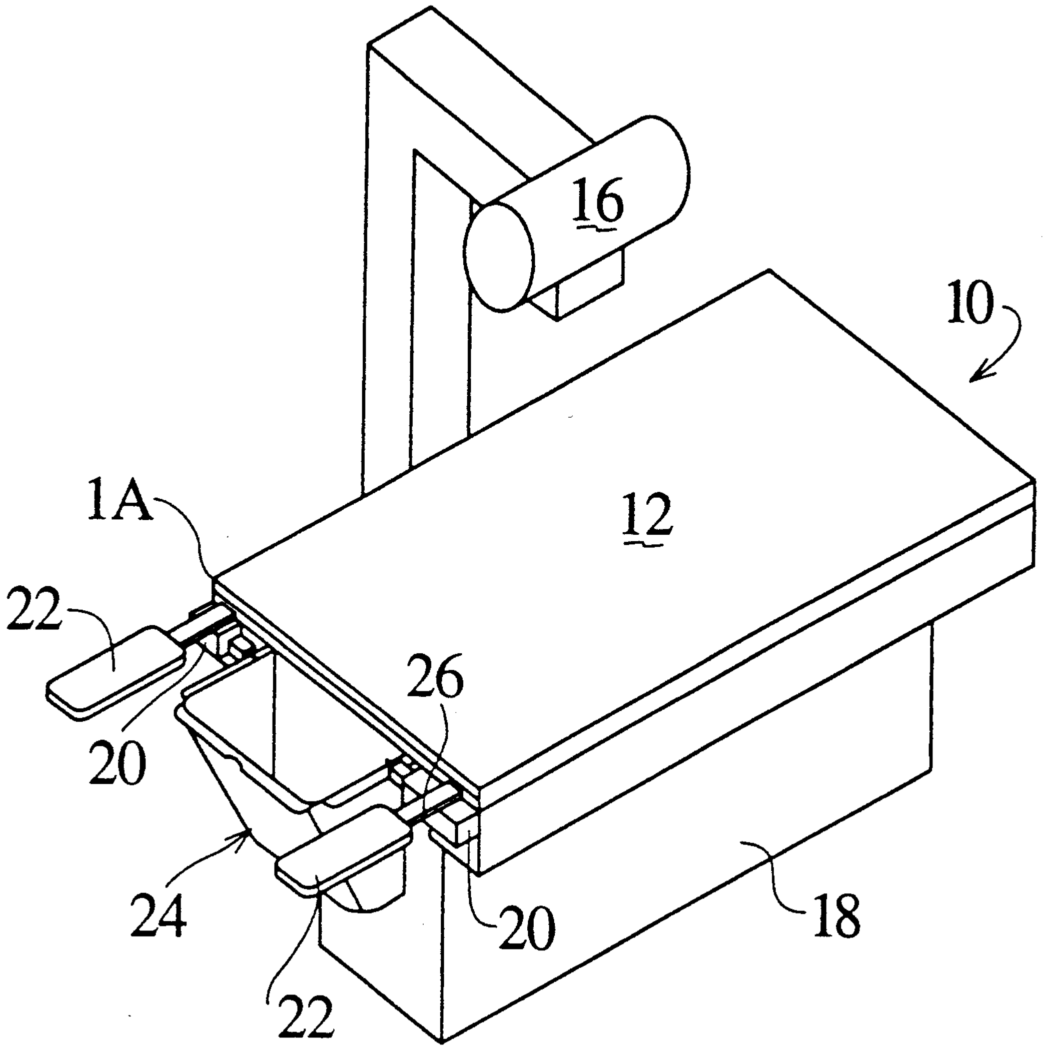
FIG. 1 is a diagrammatic illustration of a urology table and drain pan with securing means in accordance with the present invention.

With reference to FIG. 1, a urology table 10 has a patient supporting top or surface 12 that terminates toward an examination end 14. An x-ray tube or unit 16 is disposed above the patient supporting surface 12. X-ray detectors (not shown) are mounted in a table top supporting base 18 to receive radiation from the x-ray tube. In a fluoroscopy mode, low level radiation is emitted from the x-ray tube, passes through the patient and table top, and is received by the detectors. The detected radiation is converted into continuous display on a CRT or video monitor (not shown). In a radiography mode, the x-ray tube is operated at a higher energy to produce a higher contrast image either with the x-ray detectors or by exposing radiographic film.

Figure 2:
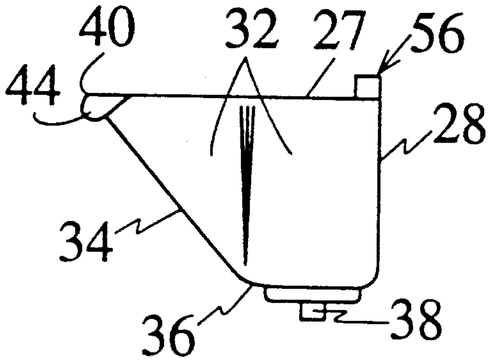
FIG. 2 is a side view of the urology drain pan assembly and securing means of FIG. 1.
Figure 3:
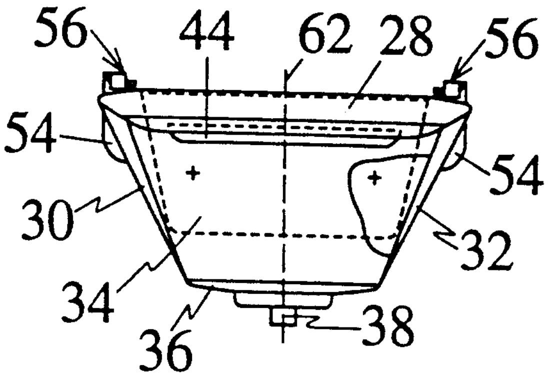
FIG. 3 is a front view of FIG. 2.
Figure 4:
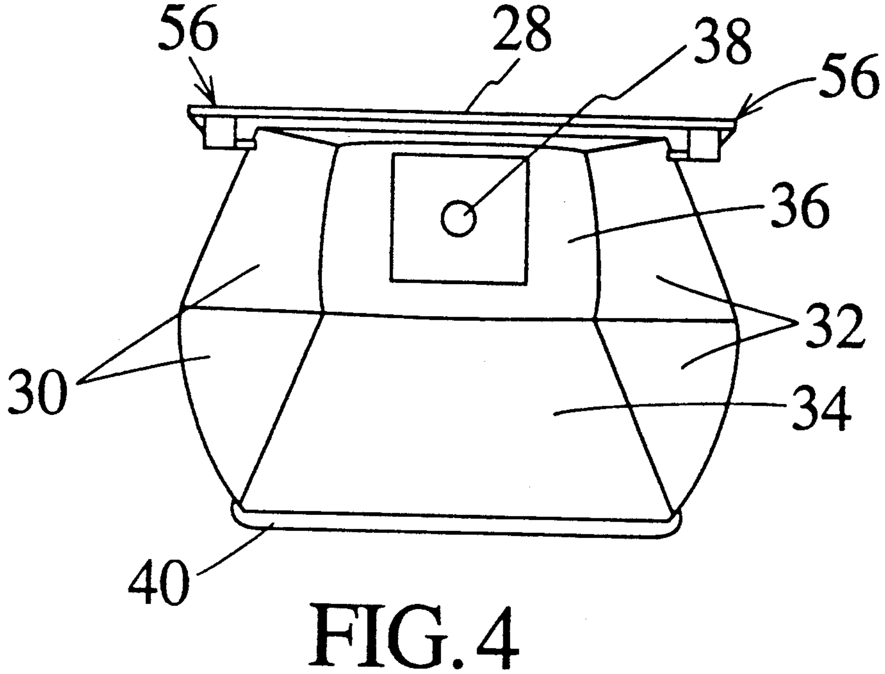
FIG. 4 is a top view of FIG. 2.

With continuing reference to FIG. 1 and further reference to FIGS. 2, 3 and 4, the urology table 10 has mounting assemblies 20 for pivotally mounting a pair of elbow supports 22 at the examination end 14 of the table. A urology pan assembly 24 is removably mounted to the examination end 14 by a drain pan mounting means 26.

The urology pan assembly further includes a drain pan or bag 27 having a generally vertical, flat inner end wall 28. A pair of side walls 30, 32 are integrally connected with the inner end wall. A sloping outer end wall 34 and a bottom wall 36 are integrally connected to the side and front walls. A drain nipple 38 is provided in the bottom wall to receive a drain hose. In the preferred embodiment, the drain pan is constructed of polyethylene although other plastics and flexible materials are contemplated.

Figure 5:
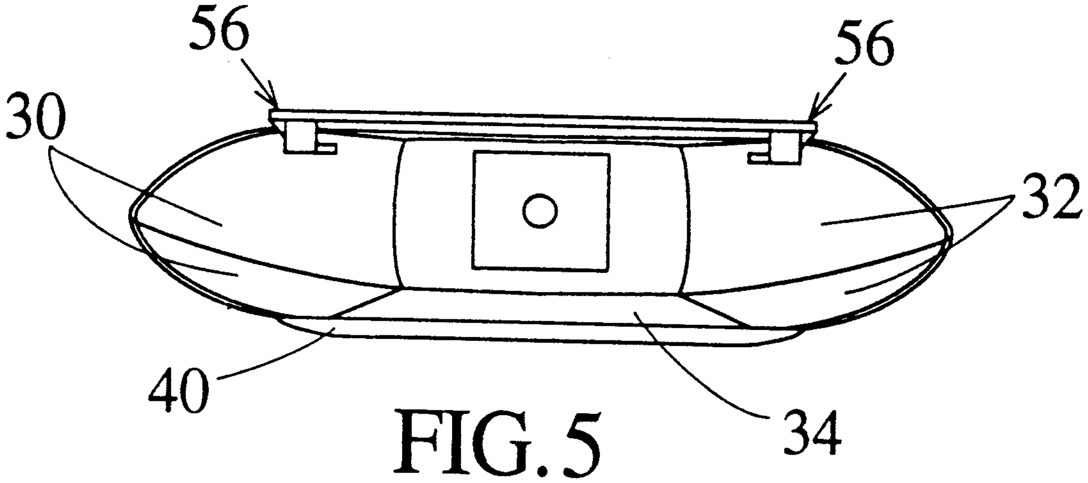
FIG. 5 is a top view showing the urology bag assembly of FIG. 4 in a partially collapsed position.

With continuing reference to FIGS. 2–4 and further reference to FIG. 5, a flange (not shown) extends outward from the top of side walls 30 and 32 and the outer end wall. The side walls and flange are configured such that the side walls can bow outward in a generally U-shaped horizontal cross section as illustrated in FIG. 5. More particularly, the horizontal side flange portions tend to flex upward and more into alignment with the side walls as the side walls are flexed. The horizontal flange stiffens a spring constant or plastic memory of the side walls and provides greater rigidity and support. The outer end wall flange 40 includes a U-shaped or rolled flange portion 44 that extends along the upper edge of the outer end wall 34. The outer wall flange portion 44 rolls downward to provide greater rigidity.

Figure 7:
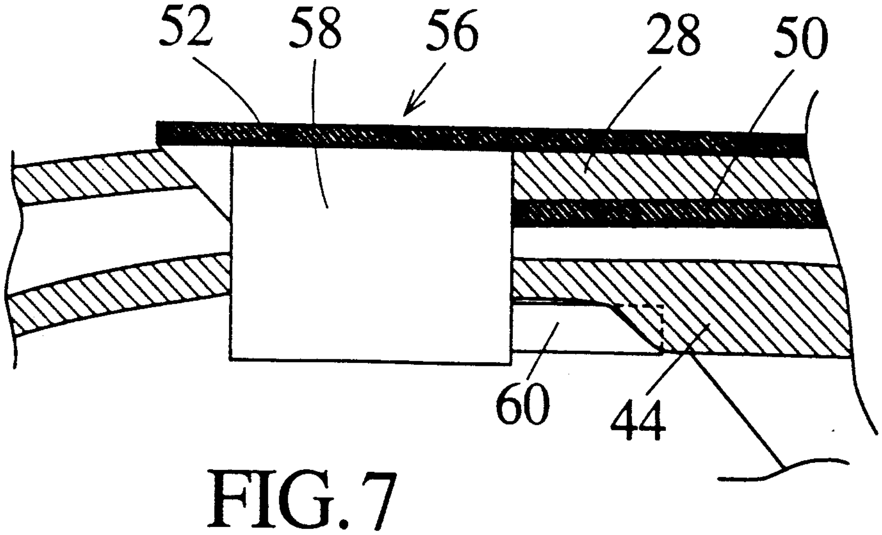
FIG. 7 is an exploded view of a portion of FIG. 6 showing the securing means in more detail.
Figure 6:
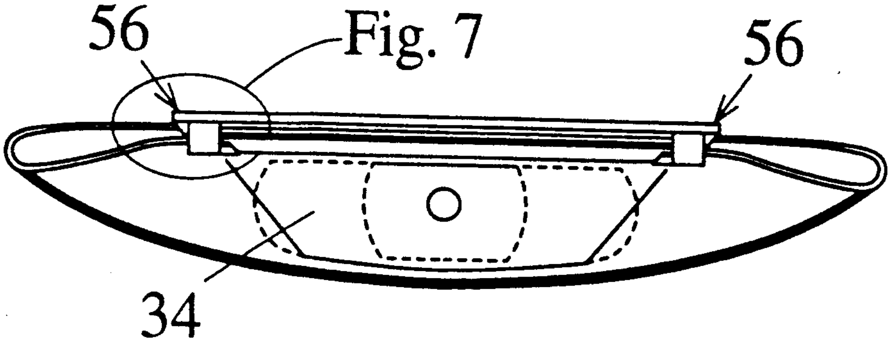
FIG. 6 is a top view of FIG. 4 showing the urology bag assembly in a fully collapsed position with the rolled outer edge engaged behind the securing means.

With continuing reference to FIGS. 1–5 and further reference to FIGS. 6 and 7, the mounting means 26 includes a pair of plates 50 and 52 which frictionally engage and lock the drain pan inner end wall 28 therebetween. The outside plate 52 includes a pair of projections or ears 54 on either end thereof which are received in matching slots (not shown) on the end face 14 of the urology table.

The outside plate 52 includes a pair of horizontal retaining means 56 fixedly secured on the upper portion of each end thereof. Each retaining means 56 is comprised of a support means 58 and retaining pin 60 arrangement. The retaining pins 60 are fixed in each end of the support means 58. Pins 60 are oriented to extend inward towards the vertical center 62 of the outside plate 52 along a line generally parallel to the upper edge of plate 52 and disposed away from inner end wall 28 a distance sufficient to allow the outer end wall 34 to be releasably held between the pins 60 and the inner wall 28.

The width of the rolled flange 44 is greater than the distance between the ends of pins 60. Therefore, if outer end wall 34 is pressed directly against inner end wall 28, the rolled flange 44 will not be engaged behind pins 60. To engage both ends of rolled flange 44 behind pins 60, a first end of flange 44 is pressed against inner end wall 28 and shifted horizontally toward its closest corresponding securing means 56. Next, a second end of flange 44 is pressed against wall 28 and shifted horizontally toward its closest corresponding securing means 56 until flange 44 is horizontally centered between pins 60 such that both ends of flange 44 are fixedly engaged by pins 60 as shown in FIG. 6. To release flange 44 from pins 60 the above process is reversed.

The drain bag 27 and retaining means 56 are designed such that the physician can secure outer end wall 34 between pins 60 and inner end wall 28 by use of the physician's elbows.

In this manner the outer end wall 34 is held in close proximity to the inner end wall when the pan apparatus is collapsed.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having described the preferred embodiment, the invention is now claimed to be:

1. A collapsible urology drain bag assembly comprising:

a collapsible urology drain bag apparatus having an outer end wall and an inner end wall, said outer end wall collapsible towards said inner end wall;

a mounting means for supporting said inner end wall in operative relation to an examination side of a urological examination table;

a retaining means having a support means comprised of a first end and a second end disposed on opposite ends of an edge of the mounting means and a retaining pin in each of both ends of the support means, said pins oriented to extend inwardly from the support means along a line generally parallel to the edge of the mounting means and disposed away from said inner wall a distance sufficient to allow said outer end wall to be releasably held between the pins and said inner end wall.

2. The assembly as set forth in claim 1, wherein the retaining means is operably connected to the mounting means.

3. The assembly as set forth in claim 1, wherein the outer end wall comprises a flange for interaction with the pins while said wall is in a collapsed, releasably held configuration.

4. The collapsible urology drain bag assembly of claim 1, wherein said drain bag apparatus is comprised of a self-supporting unitary collapsible drain bag.

5. A collapsible urology drain bag assembly comprising: a self supporting unitary collapsible drain bag having an outer end wall, a pair of integrally connected side walls, an inner end wall, said outer end wall collapsible towards said inner end wall, said walls having a memory such that as the outer end wall is pressed toward the inner end wall a spring force is provided which when the pressing force is removed caused the outer end wall to return toward its original position, an integral bottom and a drain generally opposite an upper edge of said walls;

a retaining means for releasably holding said outer end in close proximity to said inner end wall while in a collapsed configuration.

6. The assembly as set forth in claim 5 further including a mounting means for supporting the inner end wall of the drain bag in operative relation to an examination side of a urological examination table.

7. The assembly as set forth in claim 6 wherein the retaining means is operably connected to the mounting means.

8. The assembly as set forth in claim 6 wherein the retaining means includes a support means comprised of a first end and a second end disposed on opposite ends of an edge of the mounting means and a retaining pin in each of both ends of the support means, said pins oriented to allow said outer wall to be releasably held between the pins and said inner wall.

9. The assembly as set forth in claim 8 wherein the outer end wall comprises a flange for interaction with the pins while the wall is in a collapsed, releasably held configuration.

10. A collapsible urology drain bag assembly comprising: a collapsible drain bag apparatus having:

an outer end wall, an inner end wall, said outer end wall collapsible towards said inner end wall, a drain generally opposite an upper edge of said walls;

means for openly biasing the walls such that as the outer end wall is pressed toward the inner end wall a spring force is provided which when the pressing force is removed causes the outer end wall to return toward its original position;

a mounting means for coupling said inner end wall of the apparatus to an examination side of a urological examination table; and a retaining means for releasably holing the outer end wall in close proximity to the inner end wall while in a collapsed configuration.

11. The assembly as set forth in claim 10 wherein the retaining means is operably connected to the mounting means.

12. The assembly as set forth in claim 10 wherein the retaining means includes a support means comprised of a first end and a second end disposed on opposite ends of an edge of the mounting means and a retaining pin in each of both ends of the support means, said pins oriented to allow said outer wall to be releasably held between the pins and said inner wall.

13. The assembly as set forth in claim 12 wherein the outer end wall comprises a flange for interaction with the pins while the wall is in a collapsed, releasably held configuration.

14. The assembly as set forth in claim 10 wherein the drain bag apparatus is comprised of a self-supporting unitary collapsible urology drain bag.

15. A collapsible urology drain bag assembly comprising:

a self-supporting unitary collapsible urology drain bag having an outer end wall and an inner end wall, said outer end wall collapsible towards said inner end wall;

a mounting means for supporting the inner end wall in of the drain bag in operative relation to an examination side of a urological examination table; and a retaining means for releasably holding said outer end wall in close proximity to said inner end wall while in a collapsed configuration, said retaining means including a support means comprised of a first end and a second end disposed on opposite ends of an edge of the mounting means and a retaining pin in each of both ends of the support means, said pins oriented to extend inwardly from the support means along a line generally parallel to the edge of the mounting means and disposed away from said inner wall a distance sufficient to allow said outer end wall to be releasably held between the pins and said inner end wall.

16. The assembly as set forth in claim 15 wherein the outer end wall comprises a flange for interaction with the pins while the wall is in a collapsed, releasably held configuration.

17. A collapsible urology drain bag assembly comprising:

a collapsible urology drain bag apparatus having an outer end wall and an inner end wall, said outer end wall collapsible towards said inner end wall;

a mounting means for coupling said inner end wall of the apparatus to an examination side of a urological examination table; and a retaining means for releasably holding the outer end wall in close proximity to the inner end wall while in a collapsed configuration, said retaining means including a support means comprised of a first end and a second end disposed on opposite ends of an edge of the mounting means and a retaining pin in each of both ends of the support means, said pins disposed away from said inner end wall and oriented to extend inwardly from the support means along a line generally parallel to the edge of the mounting means and disposed away from said inner end wall a distance sufficient to allow said outer end wall to be releasably held between the pins and said inner end wall.

18. The assembly as set forth in claim 17 wherein the outer end wall comprises a flange for interaction with the pins while the wall is in a collapsed, releasably held configuration.

* * * * *